US009474513B2

(12) United States Patent
Ishida et al.

(10) Patent No.: US 9,474,513 B2
(45) Date of Patent: Oct. 25, 2016

(54) MEDICAL MANIPULATOR

(75) Inventors: Shinji Ishida, Kanagawa (JP); Hiroaki Sano, Shizuoka (JP); Kazuhito Ishihara, Kanagawa (JP); Keiko Kitamura, Tokyo (JP); Yoshio Hiyama, Tokyo (JP)

(73) Assignee: Karl Storz GmbH & Co. KG, Tuttlingen (DE)

( * ) Notice: Subject to any disclaimer, the term of this patent is extended or adjusted under 35 U.S.C. 154(b) by 168 days.

(21) Appl. No.: 14/129,704

(22) PCT Filed: Jun. 19, 2012

(86) PCT No.: PCT/JP2012/065582
§ 371 (c)(1),
(2), (4) Date: Mar. 26, 2014

(87) PCT Pub. No.: WO2013/002063
PCT Pub. Date: Jan. 3, 2013

(65) Prior Publication Data
US 2014/0257252 A1    Sep. 11, 2014

(30) Foreign Application Priority Data
Jun. 30, 2011 (JP) ................................. 2011-146420

(51) Int. Cl.
*A61B 17/00* (2006.01)
*A61B 17/29* (2006.01)

(52) U.S. Cl.
CPC ......... *A61B 17/00234* (2013.01); *A61B 17/29* (2013.01); *A61B 17/2909* (2013.01); *A61B 34/70* (2016.02); *A61B 2017/0046* (2013.01);
(Continued)

(58) Field of Classification Search
CPC ..................................................... A61B 19/22
USPC .............................................................. 606/1
See application file for complete search history.

(56) References Cited

U.S. PATENT DOCUMENTS 5,480,409 A * 1/1996 Riza .................... A61B 17/2909
606/205
5,779,722 A    7/1998 Shturman et al.
(Continued)

FOREIGN PATENT DOCUMENTS

JP        09-224948 A    9/1997
JP        10-174689 A    6/1998
(Continued)

OTHER PUBLICATIONS

International Search Report (PCT/ISA/210) mailed on Jul. 17, 2012, by the Japanese Patent Office as the International Searching Authority for International Application No. PCT/JP2012/065582.
(Continued)

*Primary Examiner* — Lynsey Crandall
*Assistant Examiner* — Amanda Steinberg
(74) *Attorney, Agent, or Firm* — Whitmyer IP Group LLC

(57) ABSTRACT

A medical manipulator includes a surgical tool that has an end effector at a distal end and a drive unit that is detachable from a handle of the surgical tool. In a state where the drive unit is mounted on the handle, when a manipulation lever is manipulated, a driving force of a motor is transmitted to the handle, and the end effector is operated. Even in a state where the drive unit is detached from the handle, the surgical tool can be independently used by a manual manipulation.

8 Claims, 8 Drawing Sheets

(52) U.S. Cl.
CPC ............ *A61B2017/00398* (2013.01); *A61B 2017/00734* (2013.01); *A61B 2017/2927* (2013.01); *A61B 2017/2929* (2013.01)

(56) References Cited

U.S. PATENT DOCUMENTS

| | | | |
|---|---|---|---|
| 5,792,165 A | 8/1998 | Klieman et al. | |
| 6,042,377 A * | 3/2000 | Ito | A61C 1/06 433/126 |
| 6,099,537 A | 8/2000 | Sugai et al. | |
| 2004/0092912 A1 | 5/2004 | Jinno et al. | |
| 2004/0225323 A1 | 11/2004 | Nagase et al. | |
| 2005/0103819 A1* | 5/2005 | Racenet | A61B 17/07207 227/175.1 |
| 2005/0261677 A1* | 11/2005 | Hall | A61B 18/1485 606/48 |
| 2006/0235431 A1 | 10/2006 | Goode et al. | |
| 2008/0223903 A1 | 9/2008 | Marczyk | |
| 2010/0228283 A1 | 9/2010 | Jinno | |

FOREIGN PATENT DOCUMENTS

| | | | |
|---|---|---|---|
| JP | 2001-525212 A | 12/2001 | |
| JP | 2003-024336 A | 1/2003 | |
| JP | 2003024336 A | 1/2003 | |
| JP | 2008-536577 A | 9/2008 | |
| JP | 4391762 B2 | 12/2009 | |
| JP | 2010-253205 A | 11/2010 | |
| JP | 4624696 B2 | 2/2011 | |

OTHER PUBLICATIONS

European Search Report Application No. 12803773.6 Completed: Feb. 27, 2015; Mailing Date: Mar. 5, 2015 7 pages.

* cited by examiner

MEDICAL MANIPULATOR

TECHNICAL FIELD

The present invention relates to a medical manipulator that is used when a surgical operation, particularly, an endoscopic surgical operation is carried out, and that can be operated based on a manual manipulation or based on a drive of a driving source.

BACKGROUND ART

In an endoscopic surgical operation (or, referred to as a laparoscopic surgical operation), a plurality of holes are punctured in the abdomen of a patient, trocars (tubular instruments) are inserted through the holes, and a laparoscope (camera) and a plurality of forceps are inserted into the coelom via each of the trocars. A gripper, scissors, a blade of a radio knife or the like for grasping the biological tissue or the like is attached to distal portions of the forceps as an end effector.

After the laparoscope and the forceps are inserted into the coelom, an operation is carried out by operating the forceps while observing intra-abdominal conditions displayed on a monitor that is connected to the laparoscope. In the operation method, since the abdomen is not cut open, a patient bears a small burden, and the number of days from an operation to patient recovery or patient discharge is greatly reduced. For this reason, the fields that the operation method can be applied to are expected to expand.

Other than typical forceps that are not provided with joints at distal portions, as forceps inserted through a trocar, forceps referred to as a medical manipulator have been developed that are provided with joints at distal portions and that can carry out a rolling operation or a tilting operation of an end effector (for example, refer to Japanese Patent No. 4624696 and Japanese Patent No. 4391762). According to the medical manipulator, high freedom of operation is facilitated in the coelom, a manual procedure becomes easy, and thus applicable disease cases expand.

SUMMARY OF INVENTION

As an object of reducing a manipulating force when a medical manipulator is manipulated, a motor is mounted to the medical manipulator, and an end effector of the medical manipulator is operated by a drive of the motor. However, when a configuration of a motor drive is simply adopted, reduction in the manipulating force can be achieved, whereas the weight of the medical manipulator increases. In addition, in a case where the medical manipulator is configured to be continuously operated by the motor when the motor cannot be driven due to occurrence of an event, the medical manipulator itself cannot be used.

The present invention is made in light of the problem, and an object of the present invention is to provide a medical manipulator that can suppress influence of the weight increase caused by the mounting of the driving source, and that, depending on the situation, can be used by only a manual manipulation without relying on the driving source.

In order to achieve the object, the present invention provides a medical manipulator that includes a surgical tool that has an end effector provided at a distal end, and a handle in which at least one manual manipulation portion is provided and is manipulable by a human hand, and in which the end effector is operated when a manipulating force of the manual manipulation portion is mechanically transmitted; and a drive unit that is detachable from the handle. The drive unit has unit-side manipulation portions that are manipulable by a human hand, and a driving source that is operated based on manipulation of the unit-side manipulation portions. In a state where the drive unit is mounted on the handle, the end effector is operated by a drive of the driving source.

According to the medical manipulator having the configuration, in a state where the drive unit is mounted on the handle, since the end effector is operated by a driving force of the driving source when the unit-side manipulation portion of the drive unit is manipulated, it is possible to reliably and simply operate the end effector even with a small manipulating force of the unit-side manipulation portion. In addition, even in a state where the drive unit is detached from the handle, since the end effector can be operated by manipulation of the manual manipulation portion, it is possible to detach the drive unit from the handle of the surgical tool and to make the medical manipulator light when a drive of the driving source is not necessary. Furthermore, even in a case where a problem (for example, a loss of electrical power supply or the like) occurs on a side of the drive unit during an operation, it is possible to continue to carry out the operation using only the surgical tool.

In the medical manipulator, the handle may be provided with a handle-side engagement portion. The drive unit may be provided with a unit-side engagement portion that is operated based on a driving force of the driving source. In a state where the drive unit is mounted on the handle, the handle-side engagement portion and the unit-side engagement portion may be engaged to be relatively unrotatable with each other. A driving force transmitted to the handle-side engagement portion may be transmitted to the end effector via a power transmission path that is provided in the surgical tool.

According to the configuration, power can be reliably transmitted to the end effector from the driving source of the drive unit.

In the medical manipulator, in addition to the manual manipulation portions, the handle may have an opening and closing manipulation portion that opens and closes the end effector when power is mechanically transmitted by a manual manipulation thereof. The surgical tool may include a posture changing mechanism that changes a posture of the end effector. In a state where the drive unit is mounted on the handle, the posture changing mechanism may be operated under a driving operation of the driving source based on manipulation of the unit-side manipulation portions. In a state where the handle and the drive unit are separated from each other, the posture changing mechanism may be operated based on manipulation of the manual manipulation portions.

According to the configuration, in a state where the drive unit is mounted on the handle, only a posture changing operation of the end effector can be carried out by a drive of the driving source, and an opening and closing operation of the end effector can still be carried out by a manual manipulation. For this reason, there is still an advantage in that a grasping force can be perceived when the end effector is opened and closed, and only the posture changing operation can be driven by the driving source.

In the medical manipulator, the surgical tool may include the posture changing mechanism that changes a posture of the end effector. The posture changing mechanism may carry out a rolling operation in which the end effector is rotated about an axis line thereof, and a tilting operation in which the end effector is operated in a tilting manner. The handle is provided with the two manual manipulation portions. In a state where the drive unit is mounted on the handle, notched portions may be provided in the drive unit to expose one manual manipulation portion or the other manual manipulation portion to the outside. In a state where the drive unit is separated from the handle, the rolling operation of the end effector may be carried out via a rolling operation drive shaft based on manipulation of the one manual manipulation portion, and the tilting operation of the end effector may be carried out via a tilting operation drive shaft based on manipulation of the other manual manipulation portion. In a state where the drive unit is mounted on the handle, one operation of the rolling operation and the tilting operation may be carried out under a driving operation of the driving source when a user manipulates the unit-side manipulation portions, and the other operation may be carried out when the user manipulates the manual manipulation portions via the notched portions corresponding to the other operation of the rolling operation and the tilting operation.

According to the configuration, even in a state where the drive unit is mounted on the handle, a user can touch and reliably manipulate, via the notched portions, a manual manipulation portion that corresponds to an operation of the rolling operation and the tilting operation, which is not carried out by an electric drive, that is, an operation that is carried out by a manual drive.

In the medical manipulator, the surgical tool may include the posture changing mechanism that changes a posture of the end effector. The posture changing mechanism may carry out a rolling operation in which the end effector is rotated about the axis line thereof, and a tilting operation in which the end effector is operated in a tilting manner. The handle may be provided with the two manual manipulation portions. The rolling operation of the end effector may be carried out via the rolling operation drive shaft based on manipulation of the one manual manipulation portion, and the tilting operation of the end effector may be carried out via the tilting operation drive shaft based on manipulation of the other manual manipulation portion. In a state where the drive unit is mounted on the handle, the handle furthermore may include a switching mechanism that selectively switches a switching state between a first switching state where a power transmission path is formed between the driving source and the rolling operation drive shaft and a second switching state where a power transmission path is formed between the driving source and the tilting operation drive shaft.

According to the configuration, since a target object to which a driving force of the driving source is transmitted can be selectively switched to any one of the rolling operation drive shaft and the tilting operation drive shaft, the driving source can be commonly used in the rolling operation and the tilting operation. Accordingly, only the one driving source is enough, and weight increase of the drive unit can be suppressed.

In the medical manipulator, the drive unit may be detachable in a proximal end direction of the handle.

In the medical manipulator, the unit-side manipulation portions may be provided in side portions of the drive unit. In a state where the drive unit is mounted on the handle, the unit-side manipulation portions may be positioned to overlap with the manual manipulation portion in a forward and backward direction. According to the configuration, before and after the drive unit is mounted on the handle, a manipulation position of the manual manipulation portion remains almost unchanged, and manipulability is improved.

In the medical manipulator according to the present invention, when the drive unit is mounted on the handle for use of the medical manipulator, it is possible to reliably and simply operate the end effector even with a small manipulating force. When a drive of the driving source is not necessary, it is possible to detach the drive unit from the handle and to make the medical manipulator light. Furthermore, even in a case where any problem occurs on the side of the drive unit during an operation, it is possible to continue to carry out the operation using only the surgical tool. That is, it is possible to suppress influence of the weight increase caused by the mounting of the driving source, and, depending on the situation, it is possible to use the medical manipulator by only a manual manipulation without relying on the driving source.

DESCRIPTION OF EMBODIMENTS

Hereinafter, a medical manipulator according to the present invention will be described with reference to preferred embodiments and the accompanying drawings.

[First Embodiment]

Figure 1:
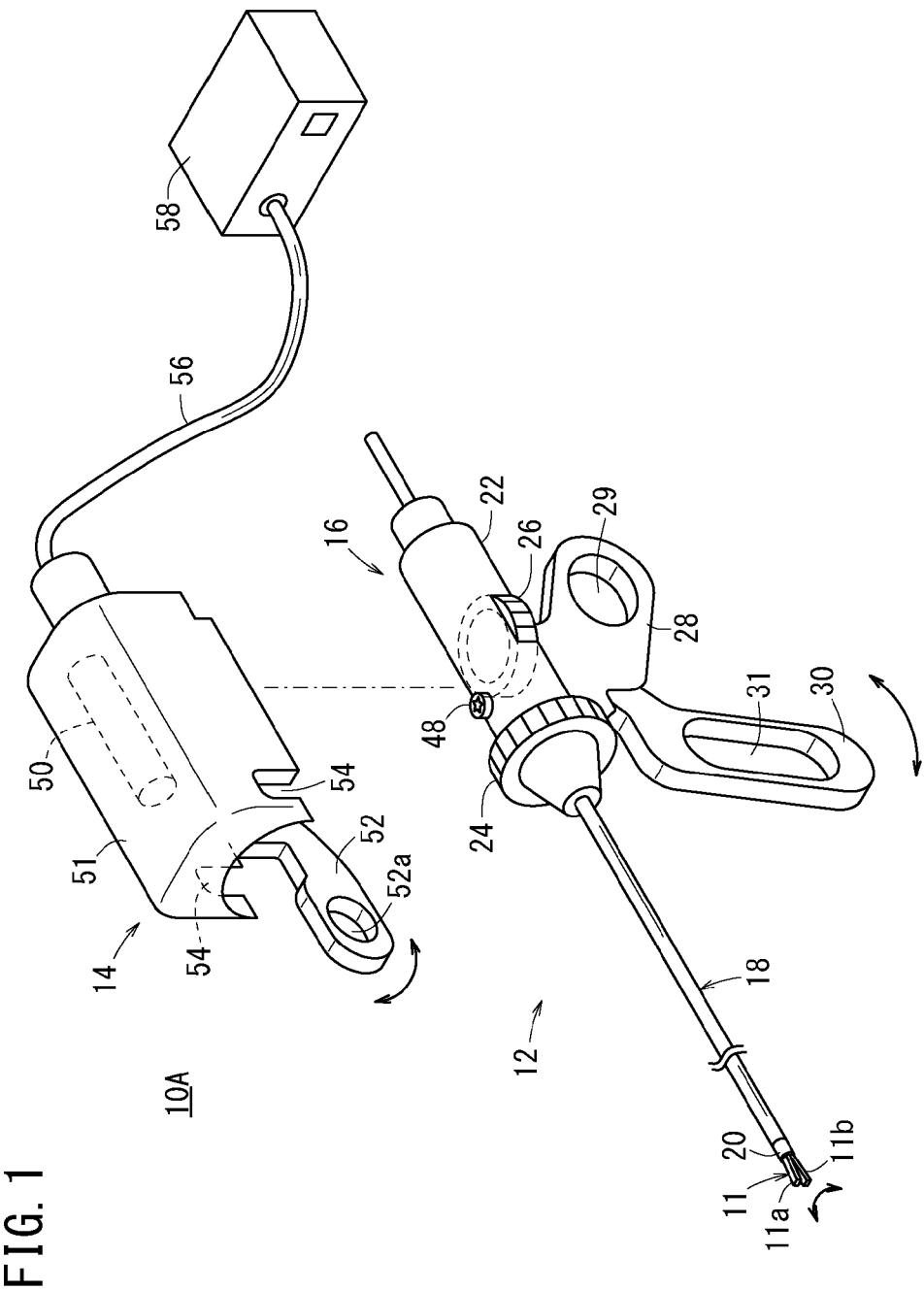
FIG. 1 is a perspective view of a medical manipulator according to a first embodiment of the present invention, and is a view illustrating a state where a surgical tool and a drive unit are separated from each other.

FIG. 1 is a perspective view of a medical manipulator 10A according to a first embodiment of the present invention. The medical manipulator 10A includes a surgical tool 12 that has an end effector 11 provided at the distal end and a drive unit 14 that is detachable from the surgical tool 12. The medical manipulator 10A is medical equipment that grasps a part of the living body or touches the living body using the end effector 11 provided at the distal end, and carries out a predetermined treatment. When the type of end effector 11 provided at the distal end is changed, the medical manipulator 10A can be configured to have grasping forceps, a needle driver, a monopolar radio knife, bipolar radio knife or the like.

The surgical tool 12 includes the end effector 11 that configures a distal portion of the surgical tool 12; a handle 16 that configures a proximal portion of the surgical tool 12 to drive the end effector 11; and a shaft (interlock portion) 18 that connects the end effector 11 to the handle 16. The end effector 11 is a portion that grasps or comes into contact with a part of the living body to carry out a surgical treatment. In the illustrated example, the end effector 11 has a pair of gripper members 11a and 11b, and is configured to have a gripper mechanism that carries out an opening and closing operation on the basis of a predetermined opening and closing operation shaft. The end effector 11 is not limited to the gripper mechanism, and may be configured to have scissors or an electrode for a radio knife.

A posture of the end effector 11 can be changed at a plurality of degrees of freedom by the function of a posture changing mechanism 20 that is provided at the distal end of the shaft 18. In the embodiment, the posture changing mechanism 20 can carry out a "rolling operation" in which the end effector 11 is rotated about an axis line of the shaft 18, and a "tilting operation" in which the end effector 11 is operated to tilt in a left and right direction (swing) with respect to the axis line of the shaft 18. In placement of a swing in the left and right direction, the tilting operation may be operation in which the end effector 11 is operated in a tilting manner in an upward and downward direction with respect to the axis line of the shaft 18.

The shaft 18 is an oblong and small diameter tubular member. A plurality of members configured to have a power transmission mechanism are inserted into or are arranged in a hollow portion of the shaft 18, and the power transmission mechanism transmits, from the handle 16 to the end effector and the posture changing mechanism 20, power that is necessary for the opening and closing operation, the rolling operation and the tilting operation of the end effector 11. A configuration of the power transmission mechanism is not particularly limited, and for example, the power transmission mechanism can adopt a configuration in which a wire, a rod or the like is used. For example, a power transmission mechanism that uses a wire, a rod or the like is disclosed in Japanese Patent No. 3421117, Japanese Patent No. 4624696, Japanese Patent No. 4226846 and the like.

The handle 16 includes a body portion 22 that is connected to a proximal end of the shaft 18; a rolling manipulation portion (manual manipulation portion) 24 and a tilting operation manipulation portion (manual manipulation portion) 26 which are provided in the body portion 22; and a gripper 28 and a trigger lever (opening and closing manipulation portion) 30 which are provided in a lower portion of the body portion 22. The rolling manipulation portion 24 in the illustrated configuration example is a ring-shaped member that is arranged to be rotatable about an axis line (the same as the axis line of the shaft 18) of the body portion 22 at a location close to a distal end of the body portion 22. When the rolling manipulation portion 24 is manually manipulated and is rotated, the rotation of the rolling manipulation portion 24 is mechanically transmitted to the posture changing mechanism 20 via a first power transmission mechanism 32 (refer to FIG. 3), and the end effector 11 is rotated about the axis line of the shaft 18.

The tilting operation manipulation portion 26 in the illustrated configuration example is a ring-shaped member that is arranged to be rotatable about an axis line in a direction orthogonal to the axis line of the body portion 22 at a location closer to a side of a proximal end than the rolling manipulation portion 24 in the body portion 22. A circumferential part of the tilting operation manipulation portion 26 is exposed from a side surface of the body portion 22. When the exposed portion is touched and is rotated by a manual manipulation, the rotation of the tilting operation manipulation portion 26 is mechanically transmitted to the posture changing mechanism 20 via a second power transmission mechanism 34 (refer to FIG. 3), and the end effector 11 is operated in a tilting manner in a direction (in the left and right direction or the upward and downward direction) that is not parallel to the axis line of the shaft 18.

Figure 3:
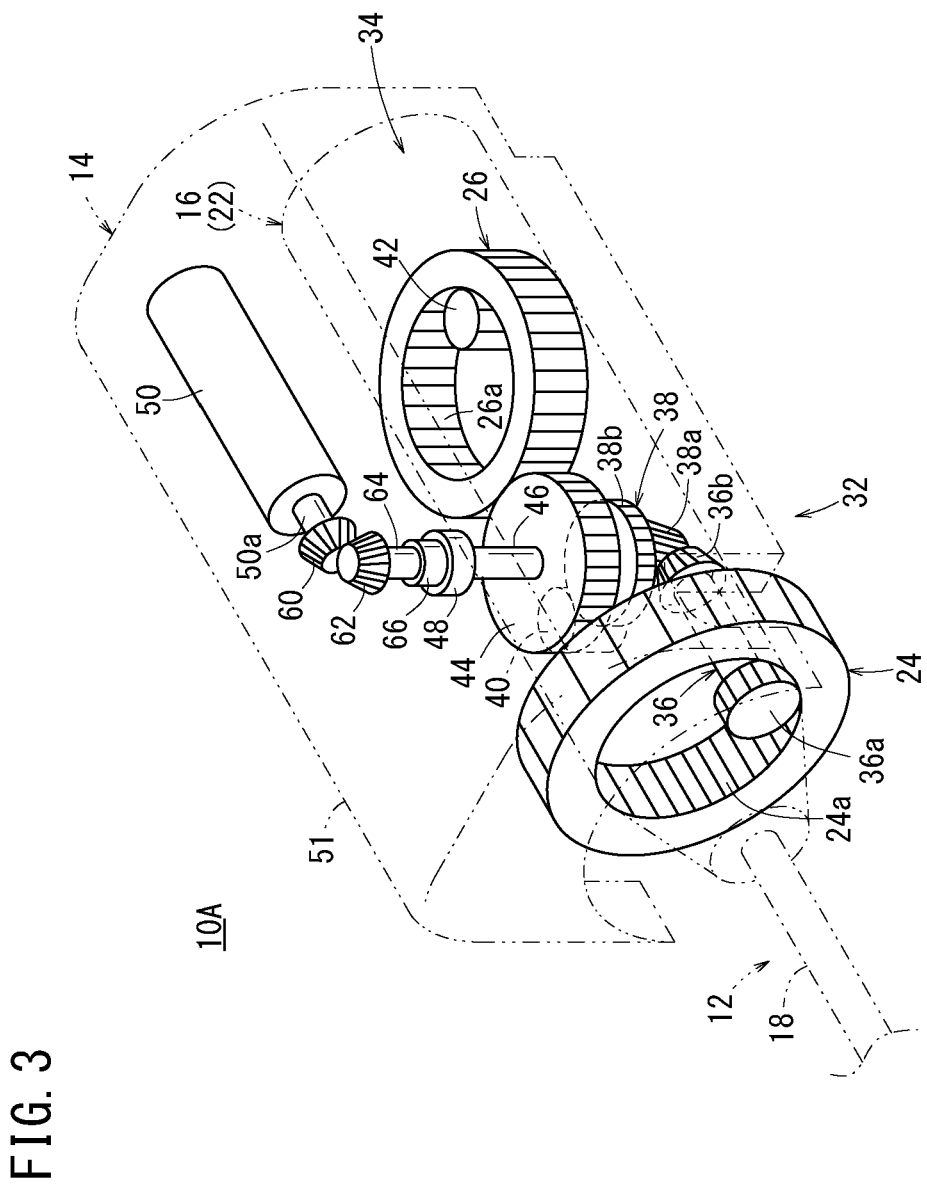
FIG. 3 is a schematic view of the drive unit and an internal mechanism of a body portion of the medical manipulator illustrated in FIG. 1.

FIG. 3 is a schematic view of the drive unit 14 and an internal mechanism of the body portion 22. As illustrated in FIG. 3, in the body portion 22, a rolling gear shaft 36 that meshes with the rolling manipulation portion 24; a gear 38 that meshes with the rolling gear shaft 36; and a rolling operation drive shaft 40 that meshes with the gear 38 (refer to FIG. 4 as well) are provided as a rolling drive transmission system. A spur gear 36a is provided on one side of the rolling gear shaft 36 (a side of the rolling manipulation portion 24) to mesh with an inner circumferential gear 24a that is provided in an inner circumferential portion of the rolling manipulation portion 24. A bevel gear 36b is provided on the other side of the rolling gear shaft 36 to mesh with the gear 38.

The gear 38 has a bevel gear 38a that meshes with the bevel gear 36b of the rolling gear shaft 36 and a spur gear 38b that is provided integrally and coaxially with the bevel gear 38a. The spur gear 38b meshes with the rolling operation drive shaft 40. Accordingly, when the rolling manipulation portion 24 is rotated by a manual manipulation, the rotation thereof is transmitted to the rolling operation drive shaft 40 via the rolling gear shaft 36 and the gear 38. A driving force transmitted to the rolling operation drive shaft 40 is transmitted to the posture changing mechanism 20 (refer to FIGS. 1 and 2) via a power transmission member (wire, rod or the like) that is not illustrated. As a result, the rolling operation of the end effector 11 is carried out. The rolling gear shaft 36, the gear 38 and the rolling operation drive shaft 40 configure a part of the first power transmission mechanism 32 that transmits power to the posture changing mechanism 20 from the rolling manipulation portion 24.

A configuration of the aforementioned first power transmission mechanism 32 is not limited to the aforementioned configuration, and another configuration can be adopted to transmit power to the posture changing mechanism 20 from the rolling manipulation portion 24.

In addition, as illustrated in FIG. 3, a tilting operation drive shaft 42 is provided in the body portion 22 to mesh with the tilting operation manipulation portion 26. The tilting operation drive shaft 42 in the illustrated example meshes with an inner circumferential gear 26a that is provided in an inner circumferential portion of the tilting operation manipulation portion 26. Accordingly, when the tilting operation manipulation portion 26 is rotated by a manual manipulation, the rotation thereof is transmitted to the tilting operation drive shaft 42 that meshes with the tilting operation manipulation portion 26. A driving force transmitted to the tilting operation drive shaft 42 is transmitted to the posture changing mechanism 20 via a power transmission member (wire, rod or the like) that is not illustrated. As a result, the tilting operation of the end effector 11 is carried out. The tilting operation drive shaft 42 configures apart of the second power transmission mechanism 34 that transmits power to the posture changing mechanism 20 from the tilting operation manipulation portion 26.

A configuration of the second power transmission mechanism 34 is not limited to the aforementioned configuration, and another configuration can be adopted to transmit power to the posture changing mechanism 20 from the tilting operation manipulation portion 26.

Furthermore, the body portion 22 has a drive gear 44 that meshes with the tilting operation manipulation portion 26; a handle-side drive shaft 46 that is coaxially connected to the drive gear 44; and a handle-side engagement portion 48 that is coaxially connected to an end portion (upper end portion in FIG. 3) on a side opposite the drive gear 44 of the handle-side drive shaft 46. The drive gear 44, the handle-side drive shaft 46 and the handle-side engagement portion 48 are integrally rotated.

Figure 2:
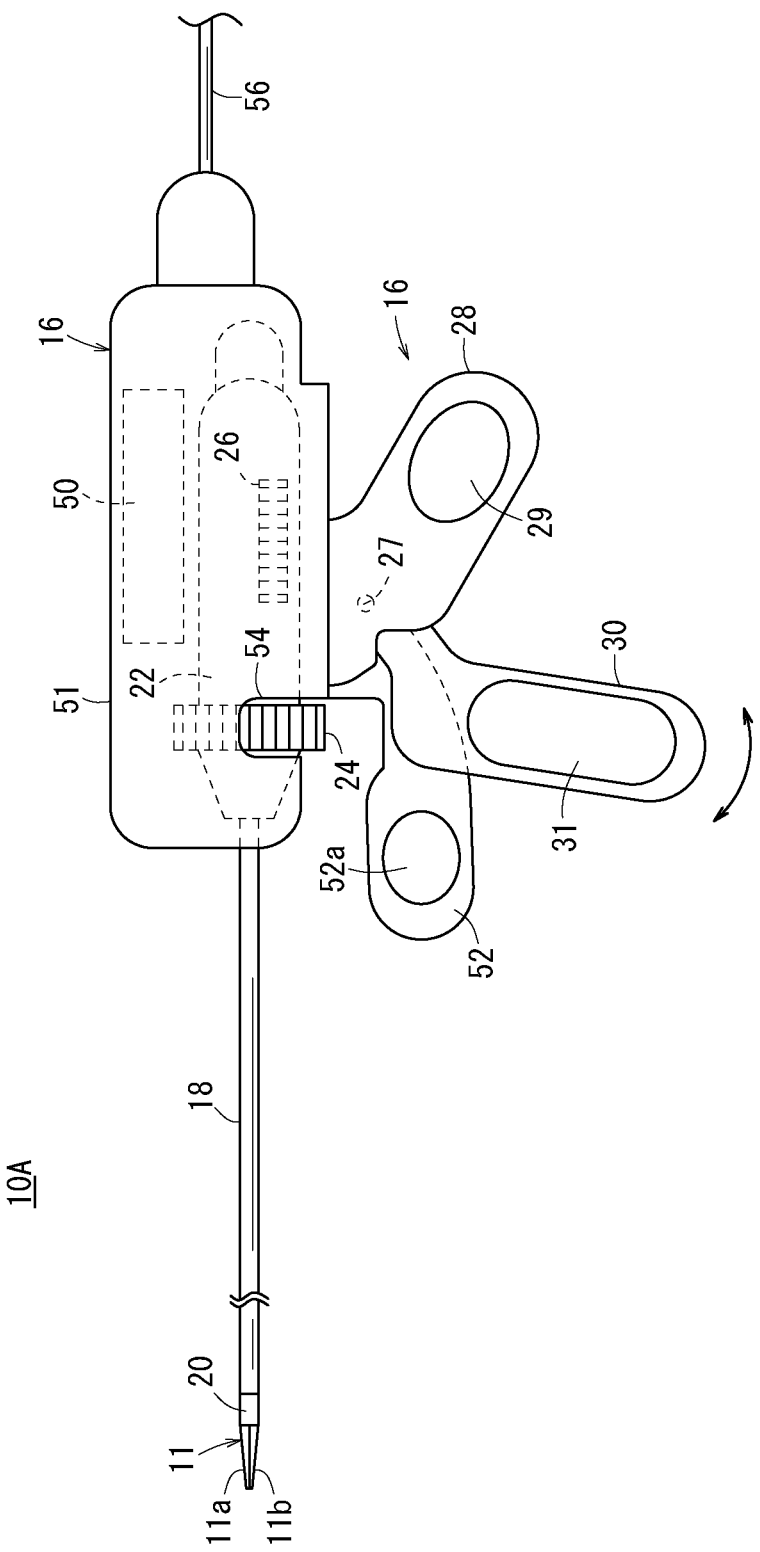
FIG. 2 is a side view of the medical manipulator illustrated in FIG. 1, in which the drive unit is mounted on the surgical tool.

The gripper 28 illustrated in FIGS. 1 and 2 is a portion that a user grasps with the fingers. The gripper 28 extends to tilt downward and backward (in the proximal end direction) from the lower portion of the body portion 22, and is provided with a finger hole 29 into which the finger (for example, thumb) is put. The trigger lever 30 is provided below the body portion 22 and in front of the gripper 28, and is swingable in the forward and backward direction about a trigger shaft 27. The trigger lever 30 is provided with a finger hole 31 into which a user's finger (for example, middle finger) is put.

An operation of the trigger lever 30 is transmitted to the end effector 11 via a third power transmission mechanism that is not illustrated. Specifically, when the trigger lever 30 is pulled backward (in the right direction in FIG. 2), the end effector 11 is closed. When the trigger lever 30 is pushed out forward (in the left direction in FIG. 2), the end effector 11 is opened. A configuration of the third power transmission mechanism is not particularly limited, and a configuration known in the related art in which a wire, a rod or the like is used can be adopted.

The drive unit 14 is configured to be detachable from the aforementioned handle 16, in particular, to the body portion 22. The drive unit 14 in the illustrated configuration example has a main unit body 51 on which a motor 50 is mounted as a driving source, and a manipulation lever (unit-side manipulation portion) 52 that is connected to the main unit body 51. The main unit body 51 is a portion that is detachable from the body portion 22 of the handle 16, the main unit body 51 has a lower side open in such a manner that the main unit body 51 can be attached to and detached from an upper side of the handle 16, and when the main unit body 51 is mounted on the handle 16, the main unit body 51 is configured to cover the most part of the body portion 22 of the handle 16.

A notched portion 54 is provided to be open downward in a side portion of the main unit body 51. For this reason, as illustrated in FIG. 2, in a state where the rolling manipulation portion 24 is mounted on the body portion 22, a part (approximately lower half portion) of the rolling manipulation portion 24 is exposed via the notched portion 54. For this reason, even in a state where the drive unit 14 is mounted on the handle 16, a user of the medical manipulator 10A can touch and manipulate the rolling manipulation portion 24 exposed from the notched portion 54.

The manipulation lever 52 is connected to be swingable in the left and right direction to the main unit body 51, and is provided with a finger hole 52a into which a user puts the finger (for example, the index finger). The manipulation lever 52 in the illustrated example extends downward from the main unit body 51, bends in the middle, and extends forward. In a state where the drive unit 14 is mounted on the handle 16, the manipulation lever 52 is provided at a position slightly offset in the left and right direction from the center of the main unit body 51 in such a manner that the manipulation lever 52 and the trigger lever 30 do not interfere with each other.

As illustrated in FIG. 1, the drive unit 14 is connected to a controller 58 via a cable 56 that includes a power line and a signal line. The controller 58 supplies electrical power to and controls a drive of the motor 50, and the controller 58 receives electrical power from an external power source. When the manipulation lever 52 is manipulated, a signal corresponding to the manipulation thereof is sent to the controller 58, and the controller 58 controls a drive of the motor 50. A part of or the entire function of the controller 58 can be integrally mounted on the drive unit 14.

As illustrated in FIG. 3, the main unit body 51 has the motor 50; a first bevel gear 60 that is fixed to an output shaft 50a of the motor 50; a second bevel gear 62 that meshes with the first bevel gear 60; a unit-side drive shaft 64 that is coaxially connected to the second bevel gear 62; and an unit-side engagement portion 66 that is connected to an end portion (lower end portion in FIG. 3) on a side opposite the second bevel gear 62 of the unit-side drive shaft 64. When the motor 50 is rotated, the rotation thereof is transmitted to the unit-side engagement portion 66 via the first bevel gear 60, the second bevel gear 62 and the unit-side drive shaft 64.

The unit-side engagement portion 66 and the handle-side engagement portion 48 can be fitted (engaged) to be relatively unrotatable with each other. For example, the unit-side engagement portion 66 can be formed in a convex portion or a concave portion which has a non-circular cross-section (for example, a corrugated cross-section, a polygonal cross-section or the like), and the handle-side engagement portion 48 can be formed in a concave portion or a convex portion which has a non-circular cross-section to conform to the convex portion or the concave portion of the unit-side engagement portion 66. When the drive unit 14 is mounted on the body portion 22 of the handle 16, the aforementioned unit-side engagement portion 66 and the handle-side engagement portion 48 are fitted to be relatively unrotatable with each other. Accordingly, the rotation of the motor 50 is transmitted to the side of the handle 16 via the unit-side engagement portion 66 and the handle-side engagement portion 48.

The medical manipulator 10A according to the embodiment basically has the aforementioned configuration, and hereinafter, an operation and effects thereof will be described.

When the medical manipulator 10A is desired to use in combination of an operation by a manual manipulation and an operation by the motor 50, the drive unit 14 is mounted on the body portion 22 of the handle 16 (refer to FIG. 2). The aforementioned unit-side engagement portion 66 and the handle-side engagement portion 48 are fitted to be relatively unrotatable with each other. Accordingly, when the manipulation lever 52 is manipulated and moved in this state, the motor 50 mounted on the main unit body 51 is driven under a controlling operation of the controller 58, a driving force of the motor 50 is transmitted to the drive gear 44 via the unit-side engagement portion 66 and the handle-side engagement portion 48. Furthermore, the driving force is transmitted to the tilting operation drive shaft 42 via the tilting operation manipulation portion 26 that meshes with the drive gear 44. Accordingly, the tilting operation of the end effector 11 is carried out.

When it is necessary to carry out the rolling operation of the end effector 11, it is preferred to rotate the rolling manipulation portion 24 by a manual manipulation. In this case, since the main unit body 51 is provided with the notched portion 54, even in a state where the drive unit 14 is mounted on the body portion 22, the part of the rolling manipulation portion 24 is exposed from the notched portion 54. For this reason, it is easy to manipulate the rolling manipulation portion 24 without interference with the main unit body 51. When it is necessary to carry out the opening and closing operation of the end effector 11, the trigger lever 30 is pushed and pulled by manual manipulation.

As described above, in the medical manipulator 10A, when the manipulation lever 52 of the drive unit 14 is manipulated in a state where the drive unit 14 is mounted on the handle 16, the end effector 11 is operated in a tilting manner by an electric drive. Accordingly, it is possible to reliably and simply operate the end effector 11 in a tilting manner even with a small manipulating force of the manipulation lever 52.

Even in a state where the drive unit 14 and the surgical tool 12 are separated from each other, the surgical tool 12 can be used as a separate body in the medical manipulator 10A. That is, in a state where the drive unit 14 is detached from the surgical tool 12, when the tilting operation manipulation portion 26 is manually manipulated (rotational manipulation), the end effector 11 can be operated in a tilting manner. Similar to the state where the drive unit 14 is mounted on the surgical tool 12, when the rolling manipulation portion 24 and the trigger lever 30 are manually manipulated, the rolling operation and the opening and closing operation of the end effector 11 can be carried out.

As such, even in a state where the drive unit 14 is detached from the handle 16, since the end effector 11 can be operated in a tilting manner by manipulation of the tilting operation manipulation portion 26, it is possible to detach the drive unit 14 from the handle 16 and to make the surgical tool 12 light when a drive of the motor 50 is not necessary. Furthermore, even in a case where any problem (for example, a loss of electrical power supply or the like) occurs on a side of the drive unit 14 during an operation, it is possible to continue to carry out the operation using only the surgical tool 12.

In the medical manipulator 10A according to the embodiment, in a state where the drive unit 14 is mounted on the handle 16, only the tilting operation of the end effector 11 can be carried out by a drive of the motor 50, and the opening and closing operation of the end effector 11 can still be carried out by a manual manipulation. For this reason, an advantage does not disappear in which a grasping force can be felt when the end effector 11 is opened and closed, only the tilting operation can be driven by the motor 50, and it is convenient to use the medical manipulator 10A.

The configuration illustrated in FIG. 3 is a configuration in which a driving force of the motor 50, which is received by the handle-side engagement portion 48, is transmitted to the tilting operation drive shaft 42 via the plurality of gears (drive gear 44 and tilting operation manipulation portion 26). However, in replacement of the configuration, for example, a configuration may be adopted in which the handle-side engagement portion 48 and the tilting operation drive shaft 42 are directly connected to each other, and a driving force is transmitted to the tilting operation drive shaft 42 without intervention of the gears.

In addition, another modification example of the embodiment may adopt a configuration in which, in a state where the drive unit 14 is mounted on the body portion 22 of the handle 16, the drive unit 14 is provided with rotary bodies (gears and the like) that come into contact with the part (for example, outer circumferential portion) of the rolling manipulation portion 24, the rotary bodies are driven by the motor 50, and the rolling manipulation portion 24 coming into contact with the rotary bodies is rotationally driven.

[Second Embodiment]

Subsequently, a medical manipulator 10B according to a second embodiment will be described with reference to FIG. 4. In the medical manipulator 10B according to the second embodiment, the same reference signs are assigned to elements that have the same or similar functions and effects to those of the elements of the medical manipulator 10A according to the first embodiment, and detailed description will be omitted. In addition, when the second embodiment is described below, with regard to configuration elements different from those of the first embodiment, "a" is added to the sign (numeral) assigned to each of the configuration elements of the first embodiment.

In a surgical tool 12a of the medical manipulator 10B according to the second embodiment, a handle 16a, particularly, an internal mechanism of a body portion 22a and a main unit body 51a are different from the internal mechanism of the body portion 22 of the surgical tool 12 and the main unit body 51 in the medical manipulator 10A (refer to FIG. 3) according to the first embodiment. As illustrated in FIG. 4, in the embodiment, a handle-side drive shaft 46a is connected to the gear 38, and is not provided with the drive gear 44 (refer to FIG. 3). Since the embodiment has the configuration, in a state where the drive unit 14a is mounted on the handle 16a, a rolling operation of the end effector 11 (refer to FIG. 1) is carried out by a drive of the motor 50.

That is, when the drive unit 14a is mounted on the body portion 22a of the handle 16a and the manipulation lever 52 (refer to FIGS. 1 and 2) is manipulated and moved, the motor 50 mounted on the main unit body 51a is driven under a controlling operation of the controller 58, and a driving force of the motor 50 is transmitted to a side of the handle 16a via the unit-side engagement portion 66 and the handle-side engagement portion 48. Furthermore, the driving force is transmitted to the rolling operation drive shaft 40 via the handle-side drive shaft 46a and the gears. Accordingly, the rolling operation of the end effector 11 is carried out.

Figure 4:
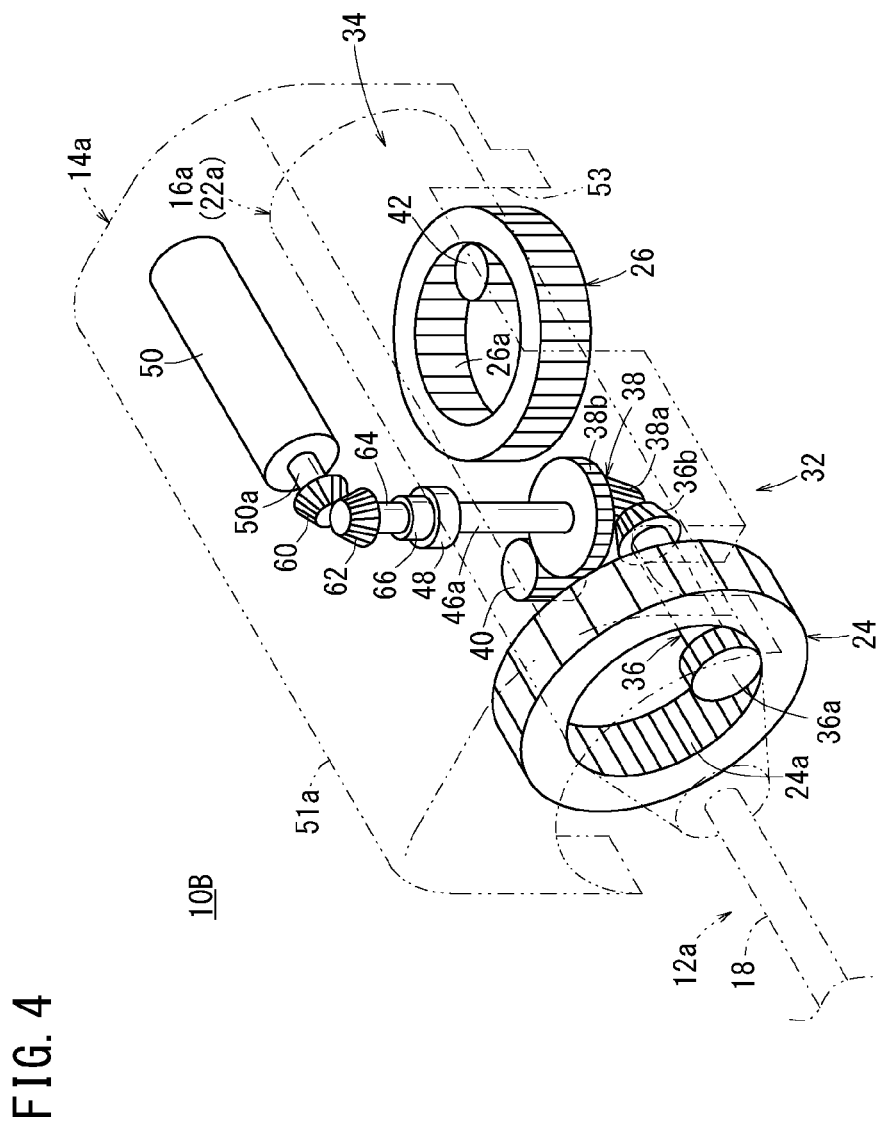
FIG. 4 is a schematic view of a drive unit and an internal mechanism of a body portion of a medical manipulator according to a second embodiment of the present invention.
Figure 5:
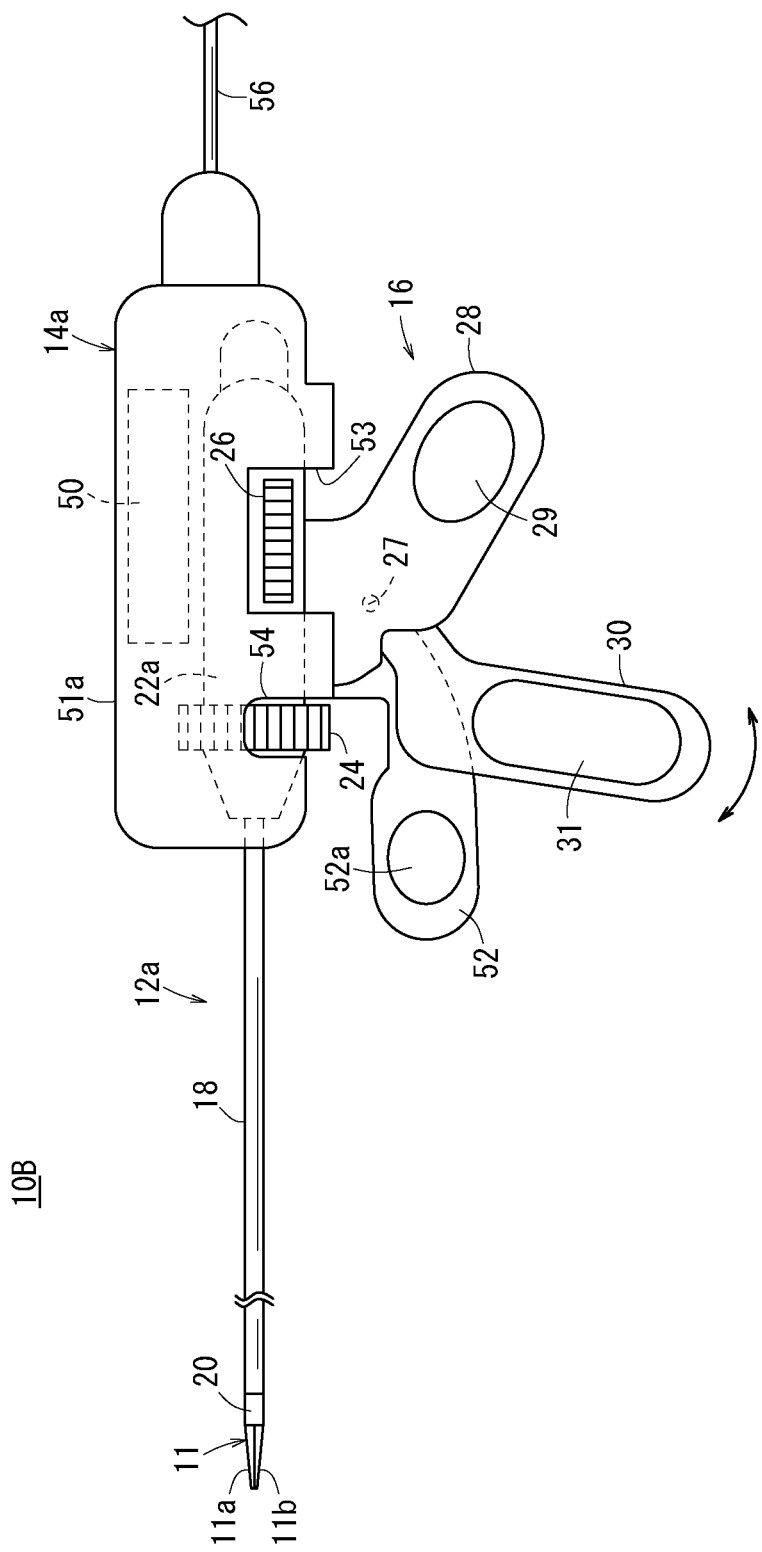
FIG. 5 is a side view of the medical manipulator illustrated in FIG. 4, in which the drive unit is mounted on a surgical tool.

As illustrated in FIGS. 4 and 5, notched portions 53 are provided in lower portions on both left and right sides of the main unit body 51a, and the tilting operation manipulation portion 26 is exposed to the outside from the notched portions 53. Since the notched portions 53 are provided, in a state where the drive unit 14a is mounted on the handle 16a, a user can touch and manipulate the tilting operation manipulation portion 26. Accordingly, even in a state where the drive unit 14a is mounted on the handle 16a, a tilting operation of the end effector 11 can be reliably carried out by a manual manipulation.

When it is necessary to carry out the tilting operation of the end effector 11, the tilting operation manipulation portion 26 is rotated by a manual manipulation.

In the medical manipulator 10B according to the embodiment, in a state where the drive unit 14a is mounted on the handle 16a, when the manipulation lever 52 of the drive unit 14a is manipulated, the rolling operation of the end effector 11 is carried out by a drive of the motor 50. Accordingly, it is possible to reliably and simply carry out the rolling operation of the end effector 11 even with a small manipulating force of the manipulation lever 52.

In a state where the drive unit 14a and the surgical tool 12a are separated from each other, the surgical tool 12a can be used as a separate body in the medical manipulator 10B. That is, in a state where the drive unit 14a is detached from the surgical tool 12a, when the rolling manipulation portion 24 is manually manipulated (rotational manipulation), the rolling operation of the end effector 11 can be carried out.

Due to the fact that an opening and closing operation of the end effector 11 can be carried out based on a manual manipulation, the medical manipulator 10B is the same as the medical manipulator 10A according to the first embodiment, and it is convenient to use the medical manipulator 10B.

In addition, in the second embodiment, with regard to each of the configuration elements in common with the first embodiment, it is needless to say that each of the common configuration elements has the same or similar operation and effects to those of the first embodiment.

The configuration illustrated in FIG. 4 is a configuration in which a driving force of the motor 50, which is received by the handle-side engagement portion 48, is transmitted to the rolling operation drive shaft 40 via the gears. However, in replacement of the configuration, for example, a configuration may be adopted in which the handle-side engagement portion 48 and the rolling operation drive shaft 40 are directly connected to each other, and a driving force is transmitted to the rolling operation drive shaft 40 without intervention of the gears.

In addition, another modification example of the embodiment may adopt a configuration in which, in a state where the drive unit 14a is mounted on the body portion 22a of the handle 16a, the drive unit 14a is provided with rotary bodies (gears and the like) that come into contact with the part (for example, outer circumferential portion) of the tilting operation manipulation portion 26, the rotary bodies are driven by the motor 50, and the tilting operation manipulation portion 26 coming into contact with the rotary bodies is rotationally driven.

In the aforementioned first and the second embodiments, only one operation of the rolling operation and the tilting operation can be carried out by a drive of the motor 50. However, the embodiments may have a configuration in which a plurality of motors are provided in such a manner that both of the rolling operation and the tilting operation can be carried out, and each of the rolling operation and the tilting operation can be carried out by a drive of each of the motors.

[Third Embodiment]

The handle 16 (16a) may be provided with a clutch mechanism (switching mechanism) in such a manner that both of a rolling operation and a tilting operation can be carried out by the one motor 50. In this case, in a state where the drive unit 14 is mounted on the handle 16 (16a), the clutch mechanism is configured to selectively switch a switching state between a first switching state where a power transmission path is formed between the motor 50 and the rolling operation drive shaft 40 and a second switching state where a power transmission path is formed between the motor 50 and the tilting operation drive shaft 42. Hereinafter, a medical manipulator that includes the clutch mechanism according to a fourth embodiment will be described.

Figure 6:
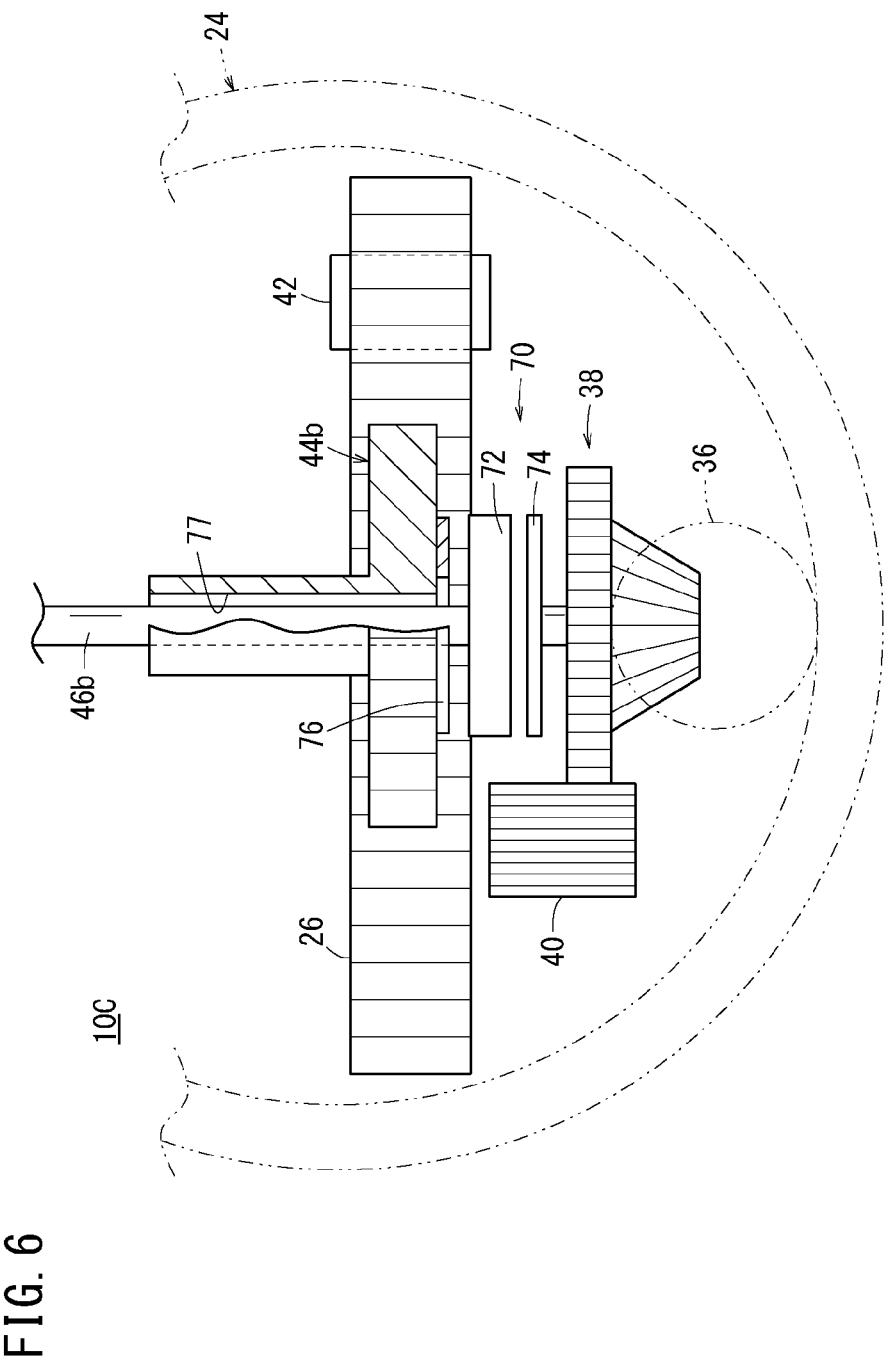
FIG. 6 is a schematic view of a drive unit and an internal mechanism of a body portion of a medical manipulator according to a third embodiment of the present invention.

FIG. 6 illustrates a clutch mechanism (switching mechanism) 70 in a configuration example of a medical manipulator 10C according to the Third embodiment. In FIG. 6, the same signs are assigned to the same configuration elements as those illustrated in FIG. 3, and with regard to configuration elements different from those illustrated in FIG. 3, "b" is added to the sign (numeral) assigned to each of the configuration elements illustrated in FIG. 3.

The clutch mechanism 70 includes a clutch disk 72 that is connected to a handle-side drive shaft 46b and is displaceable in an axial direction (in an upward and downward direction in FIG. 6); a first contacting portion (first frictional plate) 74 that is fixed (provided) to the gear 38; and a second contacting portion (second frictional plate) 76 that is fixed (provided) to a drive gear 44b. The first contacting portion 74 is provided on a side of the gear 38 which faces the drive gear 44b. The second contacting portion 76 is provided on a side of the drive gear 44b which faces the gear 38. The clutch disk 72 is arranged between the first contacting portion 74 and the second contacting portion 76, and is configured to be displaceable between a position where the clutch disk 72 comes into contact with the first contacting portion 74 and a position where the clutch disk 72 comes into contact with the second contacting portion 76.

In the configuration illustrated in FIG. 6, the handle-side drive shaft 46b is inserted into a through-hole 77 that is provided in the drive gear 44b. Accordingly, in a state where the clutch disk 72 and the second contacting portion 76 are apart from each other, the handle-side drive shaft 46b and the drive gear 44b are rotatable independently from each other. The handle 16 (refer to FIG. 1) is provided with a switch that is not illustrated and switches the position of the clutch disk 72 between the position where the clutch disk 72 comes into contact with the first contacting portion 74 and the position where the clutch disk 72 comes into contact with the second contacting portion 76.

In the clutch mechanism 70 having the configuration, when the clutch disk 72 is moved to the position where the clutch disk 72 comes into contact with the first contacting portion 74 and in this state, the handle-side drive shaft 46b is rotated by rotation of the motor 50 (refer to FIG. 1), the clutch disk 72 is integrally rotated with the gear 38 to which the first contacting portion 74 is fixed. As a result, the rotation is transmitted to the rolling operation drive shaft 40, and a rolling operation of the end effector 11 (refer to FIG. 1) is carried out. In this case, since the clutch disk 72 and the second contacting portion 76 are apart from each other, the rotation of the clutch disk 72 is not transmitted to the drive gear 44b. When it is necessary to carryout a tilting operation of the end effector 11, it is preferred to rotate the tilting operation manipulation portion 26 by a manual manipulation.

In contrast, when the clutch disk 72 is moved to the position where the clutch disk 72 comes into contact with the second contacting portion 76 and in this state, the handle-side drive shaft 46b is rotated by rotation of the motor 50, the clutch disk 72 is integrally rotated with the drive gear 44b to which the second contacting portion 76 is fixed. As a result, the rotation is transmitted to the tilting operation drive shaft 42, and the tilting operation of the end effector 11 is carried out. In this case, since the clutch disk 72 and the first contacting portion 74 are apart from each other, the rotation of the clutch disk 72 is not transmitted to the gear 38. When it is necessary to carry out the rolling operation of the end effector 11, it is preferred to rotate the rolling manipulation portion 24 by a manual manipulation.

According to the configuration of the clutch mechanism 70, since a target object to which a driving force of the motor 50 is transmitted can be selectively switched to any one of the rolling operation drive shaft 40 and the tilting operation drive shaft 42, the motor 50 can be commonly used in the rolling operation and the tilting operation. Accordingly, only the one motor 50 is enough, and weight increase of the drive unit 14 can be suppressed.

The aforementioned clutch mechanism 70 is no more than one configuration example of the switching mechanism that switches a target object driven by the motor 50 to any one of the rolling operation and the tilting operation. As another configuration example, the switching mechanism may adopt a configuration in which the gear shaft is provided to be displaceable, and the switching mechanism selectively switches a switching state between the first switching state and the second switching state by the switching of a position of the gear shaft.

[Fourth Embodiment]

Figure 7A:
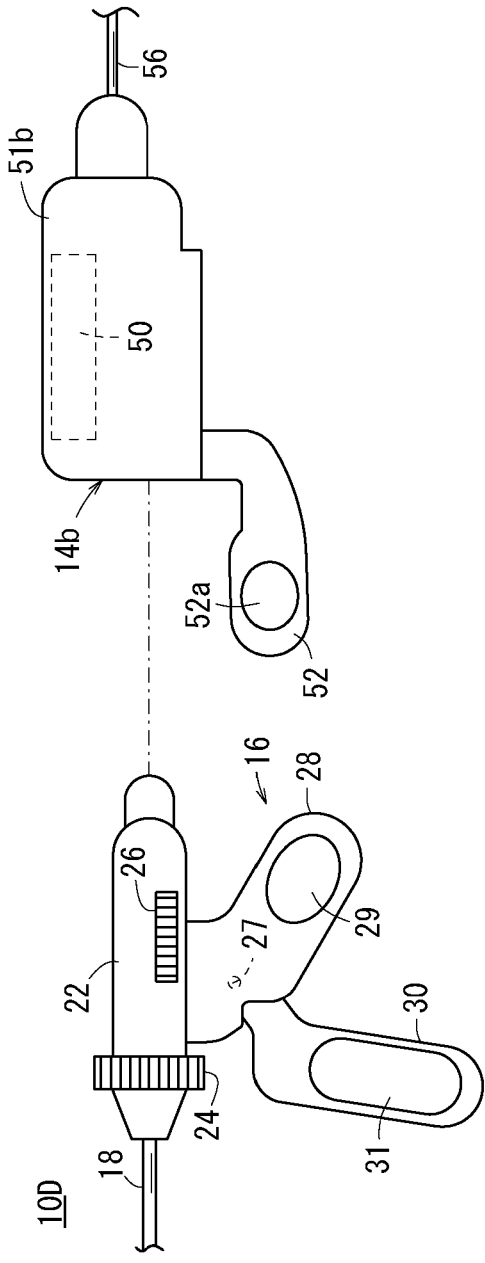
FIG. 7A is a partially abbreviated side view illustrating a medical manipulator according to a fourth embodiment of the present invention, and illustrates a state where a surgical tool and a drive unit are separated from each other.
Figure 7B:
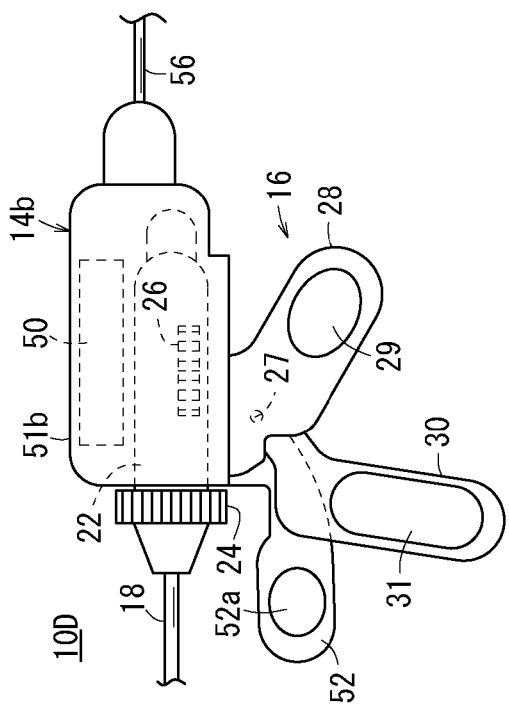
FIG. 7B is a partially abbreviated side view illustrating the medical manipulator according to the fourth embodiment of the present invention, and illustrates a state where the drive unit is mounted on the surgical tool.

Subsequently, a medical manipulator 10D according to a fourth embodiment will be described with reference to FIGS. 7A and 7B. In the medical manipulator 10D according to the fourth embodiment, the same reference signs are assigned to elements that have the same or similar functions and effects to those of the elements of the medical manipulator 10A according to the first embodiment, and detailed description will be omitted.

In the medical manipulator 10A according to the aforementioned first embodiment, the drive unit 14 has a configuration in which the drive unit 14 can be attached to and detached from the upper side of the handle 16. In contrast, in the medical manipulator 10D according to the fourth embodiment, a drive unit 14b has a configuration in which the drive unit 14b can be attached to and detached from the back side (in a proximal end direction) of the handle 16. In FIG. 7A, the drive unit 14b is detached from the handle 16, and in FIG. 7B, the drive unit 14b is mounted on the handle 16.

The main unit body 51a of the drive unit 14b is formed to have a tubular shape, and is open in a distal end direction in such a manner that the body portion 22 of the handle 16 is inserted. In a state where the main unit body 51 of the drive unit 14 illustrated in FIG. 2 and the like is mounted on the handle 16, the main unit body 51 is configured to partially cover the rolling manipulation portion 24. However, in the embodiment, as illustrated in FIG. 7B, in a state where the main unit body 51a of the drive unit 14b is mounted on the handle 16, the main unit body 51a is configured not to cover the rolling manipulation portion 24, that is, a distal portion of the main unit body 51a in the mounted state is positioned farther on a side of a proximal end than the rolling manipulation portion 24.

When the drive unit 14b is mounted on the body portion 22 of the handle 16, a driving force of the motor 50 can be transmitted to the side of the handle 16. When the internal mechanism illustrated in FIG. 3 is adopted, a driving force of the motor 50 is transmitted to the tilting operation drive shaft 42. When the internal mechanism illustrated in FIG. 4 is adopted, a driving force of the motor 50 is transmitted to the rolling operation drive shaft 40. When the internal mechanism illustrated in FIG. 6 is adopted, a driving force of the motor 50 is transmitted to the tilting operation drive shaft 42 or the rolling operation drive shaft 40 depending on an operation state of the clutch mechanism.

[Fifth Embodiment]

Figure 8:
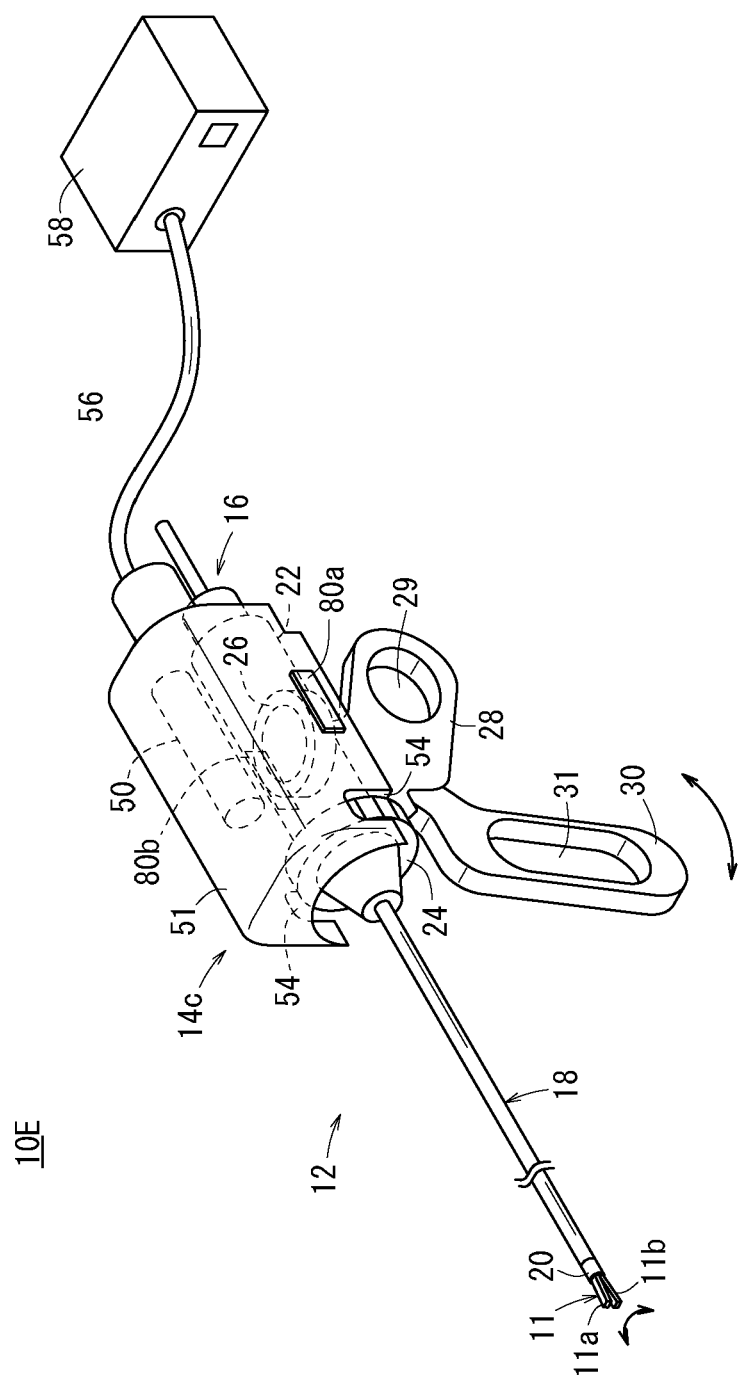
FIG. 8 is a perspective view of a medical manipulator according to a fifth embodiment of the present invention.

Subsequently, a medical manipulator 10E according to a fifth embodiment will be described with reference to FIG. 8. In the medical manipulator 10E according to the fifth embodiment, the same reference signs are assigned to elements that have the same or similar functions and effects to those of the elements of the medical manipulator 10A according to the first embodiment, and detailed description will be omitted.

The medical manipulator 10E includes the same internal mechanism as that illustrated in FIG. 3. A drive unit 14c is detachable from handle 16 of the surgical tool 12. In a state where the drive unit 14c is mounted on the handle 16, when manipulation switches 80a and 80b are manipulated, the motor 50 is driven under a controlling operation of the controller 58, and the end effector 11 is configured to be operated in a tilting manner based on a driving force of the motor 50. That is, in the embodiment, the manipulation switches 80a and 80b are configured as electric manipulation portions.

In the medical manipulator 10A according to the aforementioned first embodiment, the manipulation lever 52 of the drive unit 14 is provided on a side of a distal end of the main unit body 51. For this reason, in a state where the drive unit 14c is detached from the handle 16, when a tilting operation of the end effector 11 is carried out, a user manipulates the tilting operation manipulation portion 26. In contrast, in a state where the drive unit 14c is mounted on the handle 16, when the tilting operation of the end effector 11 is carried out, a user manipulates the manipulation lever 52 that is positioned on a side of a distal end of the handle 16.

In contrast, in the medical manipulator 10E according to the embodiment, the manipulation switches are not provided on the side of the distal end of the main unit body 51 of the drive unit 14c but on side surfaces of the main unit body 51. In a state where the drive unit 14c is mounted on the handle 16, the manipulation switches 80a and 80b are provided in the forward and backward direction (in a direction of the axis line of the shaft 18) at approximately the same position where the tilting operation manipulation portion 26 is positioned. In other words, in a state where the drive unit 14c is mounted on the handle 16, the manipulation switches 80a and 80b are positioned to overlap with the tilting operation manipulation portion 26 in the forward and backward direction.

In the medical manipulator 10E according to the embodiment, since the arrangement of the manipulation switches 80a and 80b is devised as described above, before and after the drive unit 14c is mounted on the handle 16, manipulation positions of the tilting operation manipulation portions (the tilting operation manipulation portion 26 before the mounting is carried out and the manipulation switches 80a and 80b after the mounting is completed) remain almost unchanged, and manipulability is improved.

The manipulation switches 80a and 80b in the illustrated example are provided on both left and right sides of the main unit body 51, and have rectangular shapes of which a longitudinal direction runs along the direction of the axis line of the shaft 18. When a location close to the front of the left manipulation switch 80a or a location close to the back of the right manipulation switch 80b is pressed, the controller 58 controls a drive of the motor 50 in response to the pressing manipulation, and based on the drive of the motor 50, the end effector 11 is operated in a tilting manner in a right direction when seen from a side of a user. When a location close to the back of the left manipulation switch 80a or a location close to the front of the right manipulation switch 80b is pressed, the controller 58 controls a drive of the motor 50 in response to the pressing manipulation, and based on the drive of the motor 50, the end effector 11 is operated in a tilting manner in a left direction when seen from a side of a user.

Since the embodiment has the configuration, even in a case where any one of the right manipulation switch 80a and the left manipulation switch 80b is manipulated, a user can highly sensitively manipulate the manipulation switches 80a and 80b, and manipulability is good. In addition, in any case of a case where a user grasps the gripper 28 with the right hand and of a case where a user grasps the gripper 28 with the left hand, it is possible to touch and manipulate any one of the right manipulation switch 80a and the left manipulation switch 80b with the finger suitable for ease of manipulation.

The drive unit 14c may be provided with only one of the right manipulation switch 80a and the left manipulation switch 80b. In addition, in the embodiment, each of the manipulation switches 80a and 80b is configured to be operated when a side of a main switch body 51b is pressed, but the embodiment is not limited to the configuration. Each of the manipulation switches 80a and 80b may be configured to be operated when the main switch body 51b is slid in a forward and backward direction.

[Another Embodiment]

Each of the aforementioned embodiments has a configuration in which electrical power for driving the motor 50 is supplied to the drive units 14 and 14a to 14c from the controller 58 via the cable 56. However, in replacement of the configuration, a cordless type of configuration may be adopted in which batteries (rechargeable batteries) are mounted on the drive units 14 and 14a to 14c and the cable 56 is not provided. Accordingly, it is possible to improve ease of use without interference with the cable 56.

The preferred embodiments of the present invention are described above, but the present invention is not limited to the embodiments. Various alternations can be made without departing from the spirit of the present invention.

The invention claimed is:

1. A medical manipulator, comprising:
 a surgical tool that has an end effector provided at a distal end and a handle in which at least one manual manipulation portion is provided and is manipulable by a human hand, and in which the end effector is operated when a manipulating force of the manual manipulation portion is mechanically transmitted; and
 a drive unit that is detachable from the handle, wherein
 the drive unit has a drive unit manipulation portion arranged on a main unit body of the drive unit that is manipulable by a human hand, and a driving source that is operated based on manipulation of the drive unit manipulation portion, and
 in a state where the drive unit is mounted on the handle, the end effector is operated by a drive of the driving source.

2. The medical manipulator according to claim 1, wherein the handle is provided with a handle-side engagement portion,
 the drive unit is provided with a drive unit engagement portion that is operated based on a driving force of the driving source,
 in a state where the drive unit is mounted on the handle, the handle-side engagement portion and the drive unit engagement portion are engaged to be unrotatable with each other, and
 a driving force transmitted to the handle-side engagement portion is transmitted to the end effector via a power transmission path that is provided in the surgical tool.

3. The medical manipulator according to claim 1, wherein in addition to the manual manipulation portion, the handle has an opening and closing manipulation portion that mechanically transmits power by a manual manipulation thereof, and that opens and closes the end effector,
 the surgical tool includes a posture changing mechanism that changes a posture of the end effector,
 in a state where the drive unit is mounted on the handle, the posture changing mechanism is operated under a driving operation of the driving source based on manipulation of the drive unit manipulation portion, and
 in a state where the handle and the drive unit are separated from each other, the posture changing mechanism is operated based on manipulation of the manual manipulation portion.

4. The medical manipulator according to claim 1, wherein the surgical tool includes a posture changing mechanism that changes a posture of the end effector,
 the posture changing mechanism can carry out a rolling operation in which the end effector is rotated about an axis line thereof, and a tilting operation in which the end effector is operated in a tilting manner,
 the handle is provided with Two manual manipulation portions,
 in a state where the drive unit is mounted on the handle, notched portions are provided in the drive unit to expose one of the two manual manipulation portions or the other of the two manual manipulation portions to the outside,
 in a state where the drive unit is separated from the handle, the rolling operation of the end effector is carried out via a rolling operation drive shaft based on manipulation of the one manual manipulation portion, and the tilting operation of the end effector is carried out via a tilting operation drive shaft based on manipulation of the other manual manipulation portion, and
 in a state where the drive unit is mounted on the handle, one operation of the rolling operation and the tilting operation is carried out by a driving operation of the driving source when a user manipulates the drive unit manipulation portion, and the other operation is carried out when the user manipulates the manual manipulation portions corresponding to the other operation of the rolling operation and the tilting operation via the notched portions.

5. The medical manipulator according to claim 1, wherein the surgical tool includes a posture changing mechanism that changes a posture of he end effector,
 the posture changing mechanism can carry out a rolling operation in which the end effector is rotated about an axis line thereof, and a tilting operation in which the end effector is operated in a tilting manner,
 the handle is provided with two manual manipulation portions,
 the rolling operation of the end effector is carried out via a rolling operation drive shaft based on manipulation of one of the two manual manipulation portions, and the tilting operation of the end effector is carried out via a tilting operation drive shaft based on manipulation of the other of the two manual manipulation portions, and
 in a state where the drive unit is mounted on the handle, the handle further includes a switching mechanism that selectively switches a switching state between a first switching state where a power transmission path is formed between the driving source and the rolling operation drive shaft and a second switching state where a power transmission path is formed between the driving source and the tilting operation drive shaft.

6. The medical manipulator according to claim 1, wherein the drive unit is detachable in a proximal end direction of the handle.

7. The medical manipulator according to claim 1, wherein the drive unit manipulation portion is provided in side portions of the drive unit, and in a state where the drive unit is mounted on the handle, the drive unit manipulation portion is positioned to overlap with the manual manipulation portion in a forward and backward direction.

8. A medical manipulator, comprising:
a surgical tool having:
  an end effector provided at a distal end of the surgical tool, and
  a handle having a manual manipulation portion configured to be manipulated by a human hand,
  wherein the end effector is operated when a manipulating force of he manual manipulation portion is mechanically transmitted; and
a drive unit detachably connected to the handle, the drive unit having:
  a drive unit manipulation portion arranged on a main unit body of the drive unit and configured to be manipulated by a human hand, and
  a driving source configured to be operated based on manipulation of the drive unit manipulation portion;
wherein the end effector is configured to be operated by a drive of the driving source when the drive unit is mounted on the handle.

* * * * *